US005859259A

United States Patent [19]
Sinha et al.

[11] Patent Number: 5,859,259
[45] Date of Patent: Jan. 12, 1999

[54] ACTIVATED ESTERS OF 1-PHENYLPYRAZOLIN-5-ONE FOR LABELING AMINE-FUNCTIONALIZED MOLECULES

[75] Inventors: Nanda D. Sinha, Acton; Jonathan N. Kremsky, Arlington, both of Mass.

[73] Assignee: PerSeptive Biosystems, Inc., Framingham, Mass.

[21] Appl. No.: 698,291

[22] Filed: Aug. 15, 1996

Related U.S. Application Data

[63] Continuation of Ser. No. 236,725, Apr. 29, 1994, abandoned.
[51] Int. Cl.$^6$ ...................... C07D 235/00; C07D 405/12
[52] U.S. Cl. .................................. 548/303.7; 548/364.4; 548/371.1
[58] Field of Search ............................... 548/303.7, 371.1, 548/364.4

[56] References Cited

U.S. PATENT DOCUMENTS

| | | | |
|---|---|---|---|
| 2,694,703 | 11/1954 | Graham | 260/163 |
| 4,102,857 | 7/1978 | Avar et al. | 260/45.8 |
| 4,908,453 | 3/1990 | Cocuzza | 518/113 |
| 5,233,044 | 8/1993 | Hudson | 548/110 |
| 5,247,081 | 9/1993 | Edge | 540/524 |

FOREIGN PATENT DOCUMENTS

| | | |
|---|---|---|
| 986/91 | 5/1991 | Denmark. |
| 987/91 | 5/1991 | Denmark. |
| 510/92 | 4/1992 | Denmark. |
| 0 305 201 | 3/1989 | European Pat. Off.. |
| 401797 | 12/1990 | European Pat. Off.. |
| WO 92/20702 | 11/1992 | WIPO. |
| WO 92/20703 | 11/1992 | WIPO. |
| WO 93/24507 | 12/1993 | WIPO. |
| WO 93/25706 | 12/1993 | WIPO. |

OTHER PUBLICATIONS

Chollet et al. (1995), "Biotin–Labeled Synthestic Oligodeoxyribonucleotides: Chemical Synthesis and Uses As Hybridization Probes," 13 *Nucleic Acids Res.* 1529–41.
Wilchek et al. (1988), "The Avidin–Biotin Complex In Bioanalytical Applications," 171 *Anal. Biochem.* 1–32.
Sinha et al. (1988), "The Preparation and Application of Functionalised Synthetic Oligonucleotides: III. Use of H–phosphonate Derivatives of Protected Amino–Hexanol and Mercapto–Propanol or–hexanol," 16 *Nucleic Acids Res.* 2659.
Berg et al. (1989), "Long–Chain Polystyrene–Grafted Polyethylene Film Matrix: A New Support for Solid–Phase Peptides Synthesis," 111 *J. Am. Chem. Soc.* 8024.
Bengstrom et al. (1990), "Biotinylation of Oligonucleotides Using A Water Soluble Biotin Ester," 9 *Nucleosides and Nucleotides* 123–7.
Pon, Richard T. (1991), "A Long Chain Biotin Phosphoramidite Reagent For The Automated Synthesis of 5'–Biotinylated Oligonucleotides," 32 *Tetra. Lett.* 14:1715–1718.
Nielsen et al. (Dec. 1991), "Sequence–Selective Recognition of DNA by Strand Displacement With A Thymine–Substituted Polyamide," 254 *Science* 1497–1500.
Hanvey et al. (Nov. 1992), "Antisense and Antigene Properties of Peptide Nucleic Acids,"258 *Science* 1481–1485.
Egholm et al. (1992) "Peptide Nucleic Acids (PNA). Oligonucleotide Analogues With An Achiral Peptide Backbone," 114 *J. Am. Chem. Soc.* 1895.
Egholm et al. (1992), "Recognition of Guanine and Adenine in DNA By Cytosine and Thymine Containing Peptide Nucleic Acids (PNA)," 114 *J. Am. Chem. Soc.* 9677.
Egholm et al. (Oct. 1993), "PNA Hybridizes to Complementary Oligonucletides Obeying the Watson–Crick Hydrogen Bonding Rules," 365 *Nature* 566.
Nielsen et al. (1993), "Sequence Specific Inhibiton of DNA Restriction Enzyme Cleavage by PNA," 21 *Nucleic Acids Res.* 197.
Nielsen et al. (1993), "Peptide Nucleic Acids (PNAs): Potential Anti–sense and Anti–gene Agents," 8 *Anti–Cancer Drug Des.* 53–63.
Losse et al. (1965), "Peptidsynthesen Mit O–[CBO–Aminoacyl]–Oximen Und O–[CBO–Aminoacyl]–Pyrazolon–Enolen," 684 *Justis Liebigs Analen Der Chemie* 236–242.
Garg et al. (Aug. 1975), "N$^1$Phenyl–3–Methyl–5–Pyrazolyl Esters of Possible Value In Peptide Synthesis," 83 *Chem. Abstr.*7:Abstract No. 59255d.
(1972–1976), *Chemical Substances* 9th Collective Index, vol. 76–85, pp. 17648CS and 33416CS.
(1987–1991), *Chemical Substances* 12th Collective Index, vol. 106–115, p. 95264CS.
Hudson, Derek, (1991), "Methodological Implications of Simultaneous Solid–Phase Peptide Synthesis,"114 *Chem. Abstr.*1:Abstract No. 7171n.

*Primary Examiner*—Laura L. Stockton
*Attorney, Agent, or Firm*—Testa, Hurwitz & Thibeault, LLP

[57] ABSTRACT

The disclosed invention is drawn to pyrazolinone derivatives, and methods of use thereof, for non-radioactive labeling of amine-functionalized molecules, especially biomolecules such as DNA, RNA, PNA, oligomers, carbohydrates, amino acids and peptides. Carboxyl-containing reporter groups such as biotin and fluorescein may be activated for nucleophilic addition to a primary or secondary amine moiety. Representative compounds of the invention include Dimethoxytritylbiotin-XPP, biotin-XPP, and fluorescein-XPP.

6 Claims, 11 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..15
        ( D ) OTHER INFORMATION: /note= "WHEREIN EACH XAA OF THE PNA
            SEQUENCE IS AN AMINOETHYLGLYCINE MODIFIED AS
            DESCRIBED IN THE SPECIFICATION. "

( x i ) SEQUENCE DESCRIPTION: SEQ ID NO:1:

Xaa  Xaa  Xaa  Xaa  Xaa  Xaa  Xaa  Xaa  Xaa  Xaa  Xaa  Xaa  Xaa  Xaa  Xaa
    1                      5                      1 0                      1 5

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..13
        ( D ) OTHER INFORMATION: /note= "WHEREIN EACH XAA OF THE PNA
            SEQUENCE IS AMINOETHYLGLYCINE MODIFIED AS
            DESCRIBED IN THE SPECFICATION"

( x i ) SEQUENCE DESCRIPTION: SEQ ID NO:2:

Xaa  Xaa  Xaa  Xaa  Xaa  Xaa  Xaa  Xaa  Xaa  Xaa  Xaa  Xaa  Xaa
    1                      5                      1 0

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /note= "WHEREIN EACH XAA OF THE
            PEPTIDE SEQUENCE IS MODIFIED AS DESCRIBED IN THE
            SPECFICATION"

( x i ) SEQUENCE DESCRIPTION: SEQ ID NO:3:

Ala  Asn  Lys  Gly  Xaa  Leu  Glu  Glu  Xaa
    1                      5

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
   ( A ) NAME/KEY: misc_feature
   ( B ) LOCATION: 1..20
   ( D ) OTHER INFORMATION: /label=M13-PRIMER ( x i ) SEQUENCE DESCRIPTION: SEQ ID NO:4:

AGGGTTTTCC CAGTCACGAC　　　　　　　　　　　　　　　　　　　　　　　20

ACTIVATED ESTERS OF 1-PHENYLPYRAZOLIN-5-ONE FOR LABELING AMINE-FUNCTIONALIZED MOLECULES

This is a continuation of application Ser. No. 08/236,725 filed on Apr. 29, 1994 now abandoned.

BACKGROUND

1. Field of the Invention

The detection and identification of molecules is the aim of the present application. In particular, the invention is directed to the labeling and detection of amine-functionalized biomolecules such as amino acids, oligonucleotides, carbohydrates, peptides and peptide nucleic acids with detectable marker molecules such as biotin or fluorescein by post-synthetic derivatization with marker molecule esters of 1-Phenylpyrazolin-5-one (XPP).

2. Description of the Prior Art

The need for detecting chemicals and molecules is an ongoing one in the biotechnology industry. It is a well known fact that biochemical assays and procedures in general are dependent upon the accurate identification and quantification of biomolecules, including pharmaceuticals, proteins, peptides, DNA, RNA, and PNA (Peptide Nucleic Acid). Many of these biomolecules are directly detectable by virtue of their intrinsic properties, and devices have been built to measure their ultraviolet excitation, infrared absorption, mass spectra, atomic absorption, fluorescence emission, nuclear magnetic resonance, and a host of other identifying data. However, certain classes of molecules are difficult to directly detect, and these are "labelled" with a marker molecule that is itself directly detectable.

Biomolecules are a particular class of difficult-to-detect molecules. Often they do not absorb in the ultraviolet region because of their lack of extended aromatic structures. Generally, they are not analyzable by mass spectrometry because they are too big to be rendered both ionic and volatile, and the technique requires very expensive and complex instrumentation. Infrared spectra are useful only for simple molecules. In addition, the amounts of DNA, RNA, PNA, amino acids and peptides that are present in today's sensitive recombinant assays are so low that new labels and attachment chemistries are constantly being developed in an effort to lower detection limits. Today, radioactive labels such as $^{32}P$ are used in the 5' labeling of oligonucleotides, but they have unstable shelf lives, and the attendant hazards of radiation present significant drawbacks. Thus, affinity labels such as biotin were adopted as non-radioactive labels. Biotin is strongly bound by the proteins avidin and streptavidin, which in turn may be conjugated to an enzyme such as alkaline phosphatase, or equivalently horseradish peroxidase. Addition of the avidin/streptavidin-enzyme complex to a biotin-containing target allows detection by the addition of a color indicator, which is facilitated by enzymatic reaction. In addition, biotinylated biomolecules may be extracted from a solution containing other compounds by adsorption to a streptavidin affinity column. Other non-radioactive labels include fluorescent detection by excitation of a biomolecule-fluorescer complex. Fluorescent labels such as fluorescein, coumarin, calcein, ethidium homodimer and intercalation dyes in general are common.

A variety of methods have been developed for the addition of biotin to oligonucleotides. See Wilchek, M, et al., Anal. Biochem. 171: 1–32 (1988). Chemical addition of biotin to a completed oligonucleotide is usually performed in a two-step procedure involving synthesis of an oligonucleotide modified by a primary amino group, followed by coupling, in aqueous solution, to a biotin N-hydroxysuccinimide ester. Chollet, A., et al., Nucleic Acids Res. 13:1529–41 (1985); Sinha, et al., Nucleic Acids Res. 16:2659 (1988); Bengstrom, M, et al., Nucleosides and Nucleotides 9: 123–7 (1990). Nick translation is frequently used as the enzymatic technique of choice for adding biotin to an oligonucleotide (Langer et al., Enzymatic synthesis of biotinylated polynucleotides: Novel nucleic acid affinity probes, Proc. Natl. Acad. Sci. U.S.A. 78:6633–6637 (1981).

Lately, biotin-phosphoramidite monomers have become available to take advantage of biotinylating in situ when performing automated polynucleotide synthesis. Edge, European Patent Application No. 88307934.5, discloses processes for automated synthesis of oligonucleotides in a DNA synthesizer. The polynucleotides so prepared may be used as probes for diagnostic tools in clinical diagnosis and research use. The biotin label is attached to the phosphoramidite monomer, which is then added to the growing polynucleotide chain. Similar biotin-phosphoramidite products are made by Amersham and Clontech. Recently, R. T. Pon disclosed an alternative method of making a long-chain phosphoramidite reagent for the automated synthesis of 5'-biotinylated oligonucleotides in Tetrahedron Letters 32(14): 1715–18 (1991). An N-dimethoxytritylated biotin group coupled to a 6-aminohexanol linker was converted into a phosphoramidite to yield a biotinylating reagent which can be used in automated solid phase synthesis to produce 5'-biotinylated oligonucleotides in high yields. However, in all of these biotin-phosphoramidites, the polynucleotide probe may not bind to its target sequence as well as an un-labelled probe due to the fact that the spacer-Biotin moiety now takes up the place of the omitted base, and so no base-pairing will occur where the biotin label is, affecting the hydridization characteristics. In cases where multiple labels are desired, this may be a significant drawback. In addition, some of these reagents have inadequately sized linker arms, or are insoluble in acetonitrile, a significant drawback.

Other biotinylating reagents ($N^4$-biotinylated deoxycytidine reagents) have been reported that can introduce biotin at any position. However, these reagents require lengthy and expensive synthetic procedures. See Roget, A., et al., Nucleic Acids Res. 17:7643–51 (1989); Pieles, U., et al., Nucleic Acids Res. 18:4355–60 (1990).

The use of 1-Phenylpyrazolin-5-one ("XPP") for activation of amino acid esters for solid phase peptide synthesis has been recently disclosed in U.S. Pat. No. 5,233,044 (Hudson). The '044 patent discloses the use of the enol amino acid esters of XPP for the efficient coupling of amino acids in solid-phase peptide synthesis ("SPPS"). The solid phase synthesis of peptides is a complex process which involves stepwise additions of amino-terminus-blocked amino acids to a peptide chain, the initial carboxyl terminus of which is attached to a solid support. SPPS typically begins with covalent attachment of the carboxyl end of a first alpha-amine protected amino acid through an organic linker to an insoluble resin synthesis bead. The general synthesis cycle then consists of deprotection of the alpha-amine group of the last amino acid, washing and, if necessary, neutralization, followed by reaction with a carboxyl-activated form of the next alpha-amine protected amino acid to be added. Each successive amino acid is attached to the terminal nitrogen by the carbonyl carbon of the carboxylic acid group. The '044 patent provides a unique reagent for activating amino acids for N-terminal addition, but does not disclose any method of labeling the resulting peptide.

There exists a need for more efficient and effective methods of adding non-radioactive marker molecules such as biotin and fluorescein to amine-functionalized biomolecules.

SUMMARY OF THE INVENTION

The invention is directed to a pyrazolinone derivative (XPP-reporter) having the general formula:

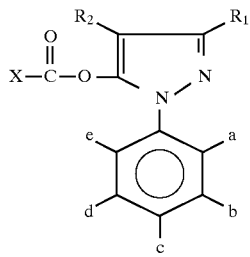

wherein: $R_1$ is selected from the group consisting of: H, methyl, ethyl, isopropyl, phenyl, nitrophenyl, chlorophenyl and benzyl; $R_2$ is selected from the group consisting of: H, methyl, ethyl, isopropyl, phenyl, nitrophenyl, chlorophenyl, benzyl, halogens, $NO_2$; a, b, c, d and e are selected from the group consisting of: H, $NO_2$, halogens and $SO_3H$; and X is a reporter molecule. Pyrazolinone derivative of formula shown above is reporter-HPP when $R_1=R_2=a=b=d=e=H$ and $c=NO_2$.

It is an object of this invention to provide a composition useful for adding reporter molecules having carboxyl groups to amine-functionalized molecules, especially biomolecules.

It is another object to make the addition of biotin and fluorescein to DNA, RNA, PNA, carbohydrates, peptides and amino acids more convenient.

It is a further object to enable one to add a reporter molecule wherever there is a primary or secondary amine on a biomolecule.

It is a further object to facilitate detection of labelled DNA, RNA, and PNA probes once hybridization to a target molecule has occurred.

These and other objects and advantages of the invention will become apparent upon review of the following disclosure, drawings and examples.

DETAILED DESCRIPTION OF THE INVENTION

The invention provides a composition and method for post-synthesis labeling of amine-functionalized molecules, especially biomolecules such as DNA, RNA, PNA, carbohydrates, amino acids and peptides. Carboxyl-containing reporter groups such as biotin and fluorescein may be activated for nucleophilic addition to a primary or secondary amine moiety. Useful compounds of the invention include dimethoxytritylbiotin-HPP (DMTr-biotin-HPP), biotin-HPP, and fluorescein-HPP.

Figure 1:
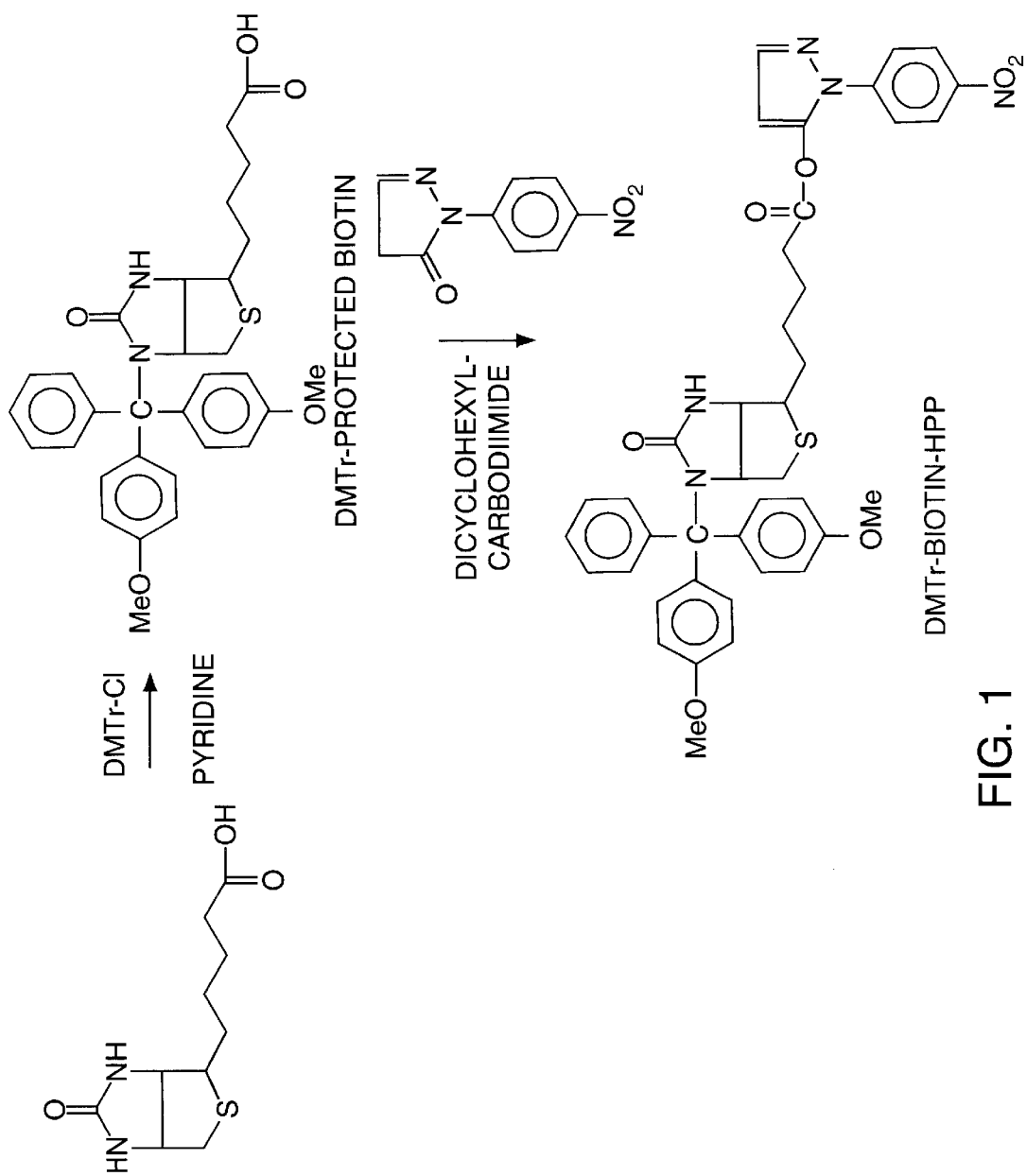
FIG. 1 is a schematic of the reaction pathway for the synthesis of DMTr Biotin-HPP.
Figure 2:
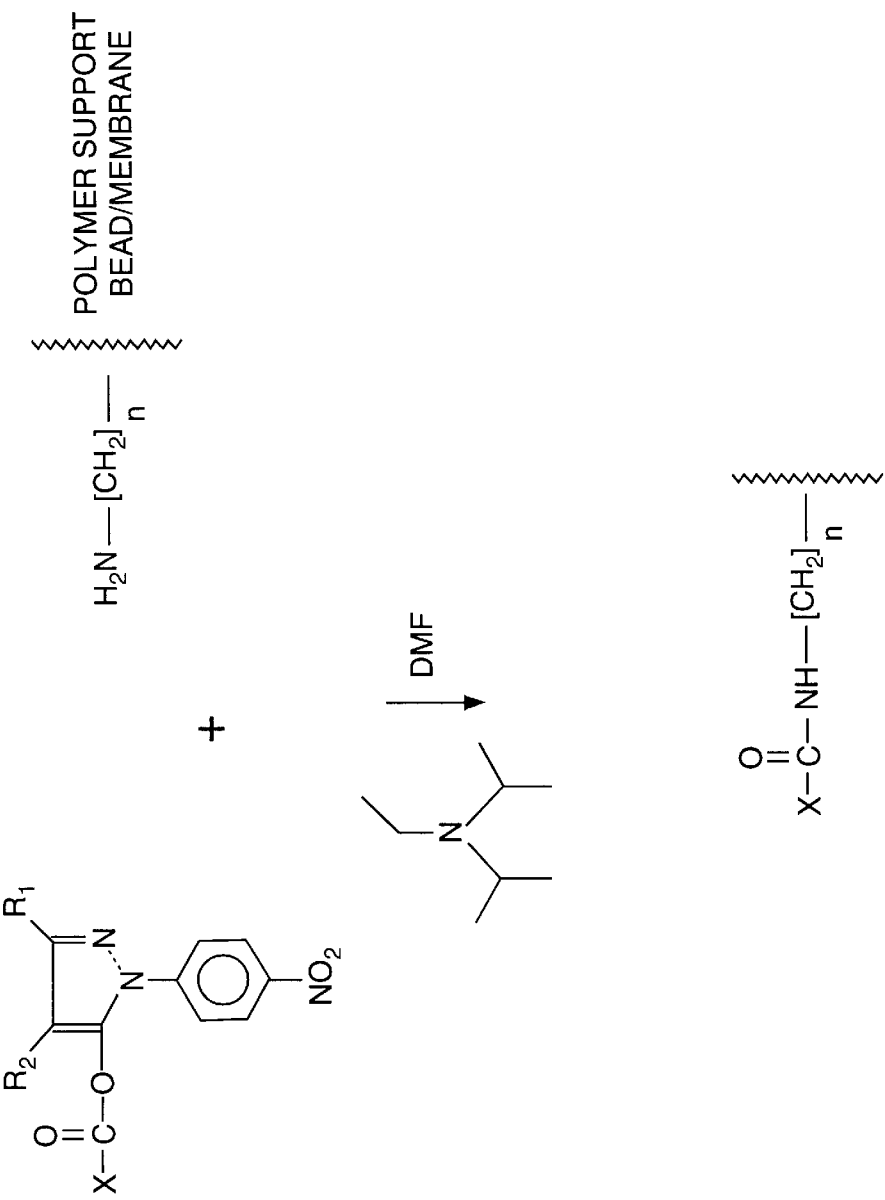
FIG. 2 is a schematic of the reaction pathway for the labelling of an N-terminal molecule attached to a polymeric support.

The general method of making the HPP-reporter composition is illustrated in FIG. 1, wherein DMTr-biotin-HPP is shown as an example. In a preferred embodiment, the starting material biotin is reacted with dimethyoxytritylchloride (DMTr-Cl) in pyridine to yield the protected DMTr-biotin molecule. This intermediate is then reacted with 1-(4'-nitrophenyl)-5-hydroxypyrazole in the presence of dicyclohexylcarbodiimide in dimethylformamide (DMF). Isolated yields are 86–90%. The XPP-adduct esters are highly crystalline solids, very stable in storage, and surprisingly selective for amines over hydroxyl groups. This latter advantage enables the efficient preparation of the desired labelled product because the XPP-adduct esters are not consumed by undesired reactions thereby depleting the reagent available for desired reactions and introducing unwanted impurities.

A specific preferred embodiment of the invention is shown in the following:

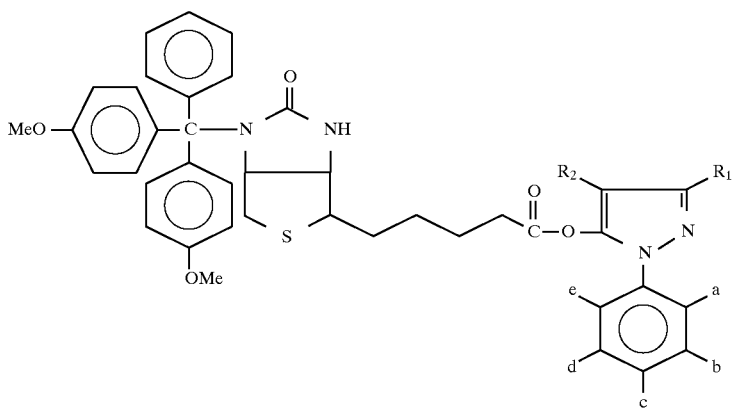

The above is a dimethoxytritylated form of biotin-XPP, also known as DMTr-Biotin-XPP. This form shows superior solubility in non-aqueous solvents such as pyridine (Example 1). Although DMTr-biotin-HPP is a preferred form of the invention, other reporter groups also come within the scope of the invention. For instance, fluorophore labels have been made such as Fluorescein-HPP disclosed in Example 2.

The fluorescein-HPP is made according to the procedure generally outlined in FIG. 1, substituting dipivaloyl-5-(6)-carboxyfluorescein for DMTr-biotin. After removal of the pivaloyl groups by base treatment, it is useful for fluorescence detection, its absorbance maximum being located at 495 nm.

The invention may be adapted to any reporter group that has or may be adapted to have a carboxyl group. Suitable reporter groups include chemiluminescent labels, fluorometric labels, and chromophoric labels. Detection can be achieved by directly labeling the biomolecule amine with a ligand as, for example, biotin, which specifically binds to the protein streptavidin, and that protein can be a carrier of a component for a chemiluminescent reaction, as for example streptavidin linked covalently to an enzyme such as alkaline phosphatase or horseradish peroxidase. All of these methods are well-known to one of ordinary skill in the art, and render the biomolecule detectably labeled.

Any biomolecule having a primary or secondary amine may be labelled and so the invention is not limited in that way. Example 4 shows the labeling of isopropylcarboxamide with DMTr-biotin, a secondary amine. Certainly, other secondary amines come within the scope of this invention.

Other labels that may be activated for addition to biomolecules include anthracene, acridine, bleomycin, benzofuran, BODIPY (4,4-difluoro-4-bora-3a,4a-diaza-s-indacene) and its derivatives, coumarin and its derivatives, digoxigenin, ethylenediaminetetracetic acid (EDTA), eosin, Lucifer Yellow, rhodamine and its derivatives, any steroid, and the sulphonated aminonapthalenes including a mixture of 1-anilinonaphthalene-8-sulfonic acid and 2-anilinonaphthaline-6-sulfonic acid (ANDA), 8-aminonaphthalene-1,3,6-trisulfonic acid (ANTS), and a mixture of 8-aminonaphthaline-1,3-disulfonic acid, 8-aminonaphthaline-1,6-disulfonic acid and 8-aminonaphthaline-3,6-disulfonic acid (ANSA). These are generally available with carboxyl groups attached, or carboxyl groups can be added by alkylation with a chloro-substituted alkanyl carboxylic acid. Commercial sources also make available many other labeling reagents that come within the scope of this application. For instance, Pierce Chemical Co., Rockford, Ill., sells a large variety of reagents for labeling molecules. These and other sources are well known to those of ordinary skill in the art.

Addition of a carboxyl group by alkylation with a chloro-substituted alkyl bearing a carboxyl is also well-known. One method of accomplishing this alkylation is by reacting the marker molecule containing a reactive group such as a hydroxy (OH) or amine ($NH_2$) with a terminally-substituted alkyl such as 1-chlorobutanoic acid, or an ester thereof, in a non-aqueous solvent such as DMF or tetrahydrofuran (THF). A base such as sodium hydride is used as a proton abstractor to initiate the reaction.

The use of activated XPP esters of reporter molecules to label amine-functionalized biomolecules is demonstrated in Examples 3, and 5–6 which show the labeling of peptide nucleic acids, peptides, and DNA oligonucleotides with biotin or fluorescein-HPP. In particular, Example 3 shows the N-terminal labeling of a PNA oligomer with DMTr-biotin-HPP and Fluorescein-HPP. Example 5 shows the labelling of the Prothrombin peptide with both reagents. And, Example 6 demonstrates the amine-specific labeling of DNA (M13) with Fluorescein-XPP.

Having now generally described this invention, the same will become better understood by reference to certain specific examples which are included herein for purposes of illustration only and are not intended to be limiting unless otherwise specified. All patents and publications cited herein are fully incorporated by reference in their entirety.

EXAMPLES

Example 1

Synthesis of DMTr-HPP Biotin

I. Dimethoxytritylation of Biotin

A clean, dry 3 liter (L) round bottom flask was equipped with a large stirring bar. Biotin (USP grade, Roche Vitamins and Fine Chemicals, Code 63345-003) (50 gram (gm.), 205 mmol, 1 eq.) was co-evaporated with 1 liter anhydrous pyridine. The solid was re-suspended in 2.5 L pyridine and treated with DMAP (12.25 gm, 10.2 mmol, 0.05 eq.) and 4,4'-dimethoxytrityl chloride DMTr-Cl (152 gm., 450 mmol, 2.2 eq.). The resulting mixture was stirred at room temperature. The reaction should be allowed to proceed for at least 24 hours.

The reaction mixture was concentrated to a paste and the residue taken up in 1 L dichloromethane $CH_2Cl_2$. The solution was washed with 200 mL saturated sodium bicarbonate. Repeat as needed until no more $CO_2$ gas is produced. The bicarbonate wash was followed by two washes with water, and finally brine. The organic layer was dried over anhydrous sodium sulfate, filtered and evaporated to dryness to afford 195 gm solid. Some insoluble material may remain at the interface between the organic and the aqueous layers, which is found to be biotin. In the case described here, the recovered biotin (15.4 gm) represents 30% of the added starting material.

The solid was purified by preparative chromatography on silica. The sample was dissolved in 900 mL $CH_2Cl_2$ and the column eluted with $CH_2Cl_2$ until the excess 4'4'-dimethoxytritylalcohol began to elute. The sample was bumped to 10% $MeOH/CH_2Cl_2$, then 20% $MeOH/CH_2Cl_2$. This purification was almost like a one-plate separation, and the product was collected in four fractions. Evaporation to dryness yielded 70 gm pure DMT-biotin (90% based on recovered starting material). Proton NMR data: (DMSO-$d_6$) 7.2–6.8 (Ar, m, 13H ); 6.8 (NCON$\underline{H}$CH, s, 1H); 4.3 (bridgehead C$\underline{H}$, m, 2H); 3.75 ($OCH_3$, s, 6H); 3.2–3.0 (C $\underline{H}_2$SC$\underline{H}$, m, 3H); 2.2 (C$\underline{H}_2CO_2H$, bd s, 2H); 1.7–1.2 ((C $\underline{H}_2)_3$, m, 6H,).

II. Synthesis of DMTr-biotin-HPP

A solution of 10 gm (18.4 mmol, 1 equiv.) DMTr-biotin in 150 mL anhydrous N,N'-dimethylformamide was treated with 4.2 gm. (20.2 mmol, 1.1 equiv.) N,N-dicyclohexylcarbodiimide (DCCI) and 3.9 gm ( 20.2 mmol, 1.1 equiv.) 1-(4'-nitrophenyl)-5-hydroxypyrrazoline (HPP) (See U.S. Pat. No. 5,233,044 (Hudson) for synthesis of HPP generally) and the mixture was stirred at room temperature for 18 hours. The solid dicyclohexylurea is removed by filtration and the solids washed with ethyl acetate. The solvent was evaporated and the residue taken up in ethyl acetate. The organics were washed with water and brine, dried over sodium sulfate, filtered, and concentrated to dryness. The resulting solid was purified by preparative chromatography with silica using a gradient of 0–10% methanol in chloroform. Trityl active fractions were collected and evaporated to give 9.4 gm (71%) HPP-ester. Proton NMR data: ($CDCl_3$): 8.35 (d, 2h, Ar, m); 7.85 (d, 2H Ar,); 7.67 (d, 1H, H-3); 7.3–6.8 (m, Ar); 6.4 (d, 1H, H-4); 5.3 (s, 1H, CON$\underline{H}$); 4.3 (2m, 2H, bridgeheads); 3.8 (s, 6H, ($OCH_3)_2$); 3.05 (m, 1H, SC$\underline{H}$); 2.5 (t, 2H, C$\underline{H}_2CO_2$); 2.4 (m, 1H, $\underline{H}$CHS); 2.25 (dd, 1H HC$\underline{H}$S); 1.6–1.2 (m,-$(CH_2)_3$-). IR band for the activated biotin-HPP ester: The DMTr-biotin has a carboxyl band at 1790 $cm^{-1}$. The HPP ester has the carbonyl band at 1695 $cm^{-}$. (KBr disks, on a Nicolet FTIR Model 5PC.)

Example 2

Synthesis of Dipivaloylfluorescein-HPP

Dipivaloylfluorescein-HPP (shown below) was prepared from (3,4)carboxyfluorescein (Eastman) with pivaloyl chloride (Theisen, et al., Tet. Letters, 33, 5033 (1992)). This was converted to its HPP ester under the conditions reported for the biotin analog. The NMR spectrum is a series of overlapping aromatic multiplets, and the assignments below are subject to change. $^1$H NMR ($CDCl_3$): 8.8 (meta, s, 1H, H5); 8.3 (H3, 1H, HPP); 8.2 (m, meta+para); 7.8 (d, H4, 1H, HPP); 7.7 (m, meta+para); 7.3 (d, 2H, meta); 7.1 (m, meta+para); 6.8 (m, meta+para); 6.6 (m,para); 1.36 (s, 18H, $CH(CH_3)_3$).

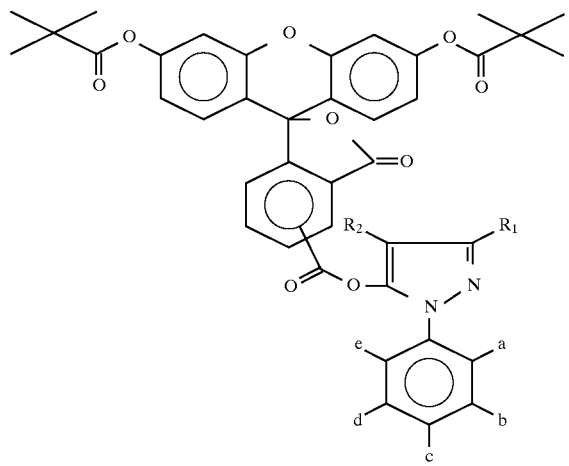

wherein $R_1=R_2=a=b=d=e=H$ and $c=NO_2$.

Figure 6:
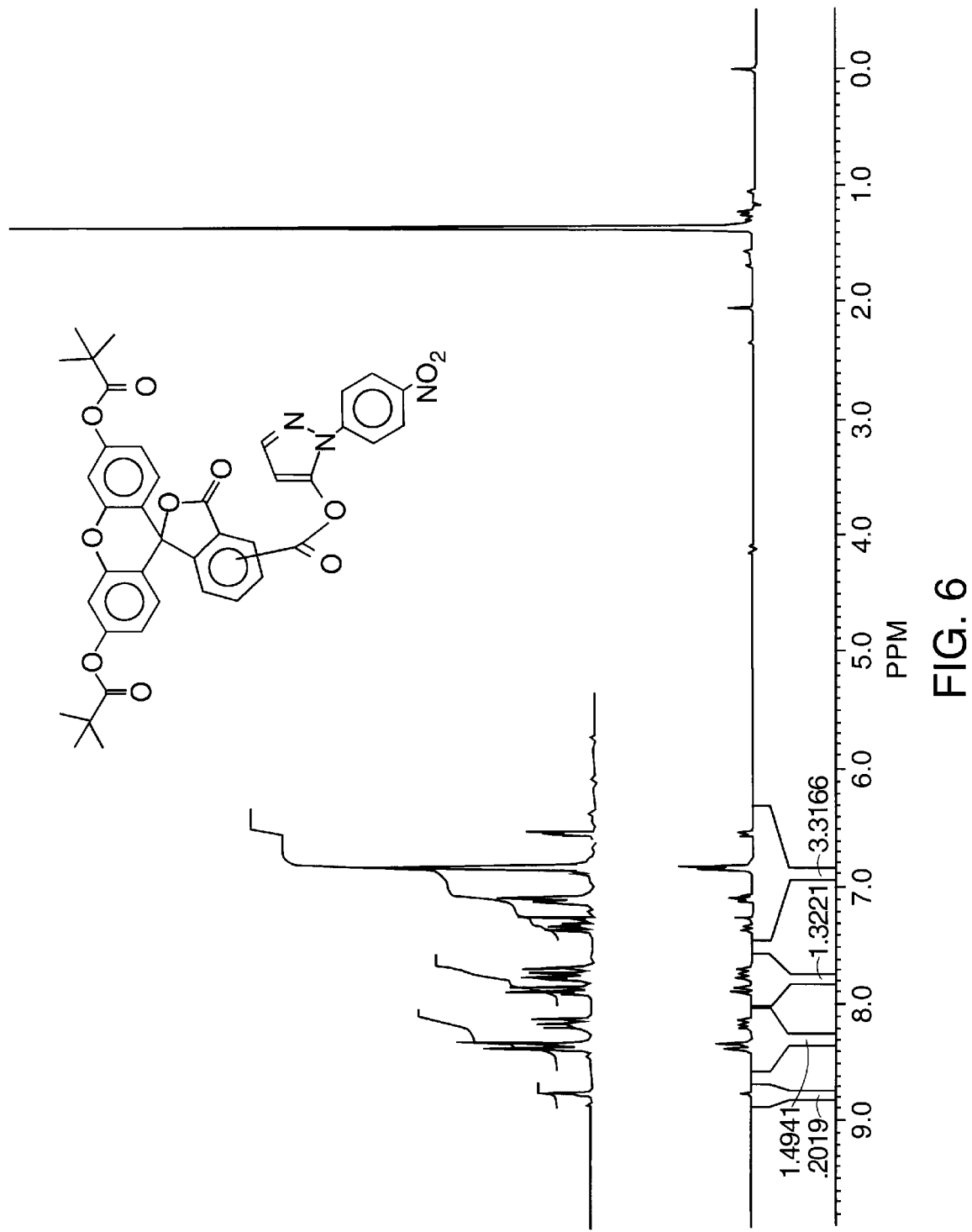
FIG. 6 is an NMR spectrum of Dipivaloylfluorescein-HPP.

The NMR spectrum of the above compound is shown in FIG. 6.

TABLE 1

| Example No. | Exemplary Molecule | SEQ. ID No. | Sequence Type | Sequence Description | Sequence Features |
|---|---|---|---|---|---|
| 3 | PNA (Peptide Nucleic Acid) | 1 | Amino Acid | $(Xaa)_{15}$ | wherein each Xaa is aminoethylglycine; wherein the N-terminus of $Xaa_1$ is labelled with DMTr-Biotin-XPP; wherein $Xaa_1$ $Xaa_3$ $Xaa_4$ $Xaa_5$ $Xaa_8$ are modified witn the nucleobase Thymine attached to N-acetyl(2-aminoethyl)glycine via the N-acetyl group at position 1 of the base; wherein $Xaa_2$ $Xaa_6$ $Xaa_7$ $Xaa_{12}$ $Xaa_{15}$ are modified with the nucleobase Adenine attached to N-acetyl(2-aminoethyl)glycine via the N-acetyl group at position 9 of the base; wherein $Xaa_9$ $Xaa_{10}$ $Xaa_{11}$ are modified with the nucleobase Cytosine attached to N-acetyl(2-aminoethyl)glycine via the N-acetyl group at position 1 of the base; wherein $Xaa_{13}$ $Xaa_{14}$ are modified with the nucleobase Guanine attached to N-acetyl(2-aminoethyl)glycine via the N-acetyl group at position 9 of the base; wherein $Xaa_{15}$ has a C-terminal amide. |
| 3 | PNA (Peptide | 2 | Amino Acid | $(Xaa)_{13}$ | wherein each Xaa is aminoethylglycine; wherein the N-terminus of $Xaa_1$ is unlabelled or labelled with Fluorescein |

TABLE 1-continued

| Example No. | Exemplary Molecule | SEQ. ID No. | Sequence Type | Sequence Description | Sequence Features |
|---|---|---|---|---|---|
| | Nucleic Acid) | | | | XPP; wherein $Xaa_1$ $Xaa_2$ $Xaa_4$ $Xaa_5$ $Xaa_6$ $Xaa_7$ $Xaa_8$ $Xaa_{11}$ $Xaa_{12}$ are modified with the nucleobase Cytosine attached to N-acetyl(2-aminoethyl)glycine via the N-acetyl group at position 1 of the base; wherein $Xaa_3$ is modified with the nucleobase Adenine attached to N-acetyl(2-aminoethyl)glycine via the N-acetyl group at position 9 of the base; wherein $Xaa_9$ $Xaa_{10}$ $Xaa_{13}$ are modified with the nucleobase Thymine attached to N-acetyl(2-aminoethyl)glycine via the N-acetyl group at position 1 of the base; wherein $Xaa_{13}$ has a C-terminal amide. |
| 5 | Peptide | 3 | Amino Acid | Ala-Asn-Lys-Gly-$Xaa_1$-Leu Glu-Glu-$Xaa_2$ | wherein Alanine at position 1 has an amino terminus; wherein $Xaa_1$ is Tyr (OAl), wherein the phenol of Tyroamine is protected with an alyl group; wherein $Xaa_2$ is Val($NH_2$), wherein Valine has a C-terminal amide. |
| 6 | DNA | 4 | Nucleic Acid | AGGGTT-TTCC-CAGTC-ACGAC | M13 primer |

Example 3

N-terminal labeling of a PNA sequence with Biotin- and Fluorescein-XPP

The use of the XPP active esters of Biotin and Fluorescein to label Peptide Nucleic Acid (PNA) oligomers was demonstrated in this example.

Methodology. Peptide nucleic acid (PNA) was synthesized on a polyethyleneglyco/(PEG)-polystyrene support material using modified t-BOC chemistry as described by Christensen, Lief, et al., *Innovation and Perspectives in Solid Phase Synthesis and Complementary Technology- Biological and Biomedical Applications,* 3d SPS Oxford Symposium Series, 1994 [in press]. A PNA sequence, Biotin-[linker]2-TATTTAATCCCAGGA-CONH2 (SEQ ID No. 1), was synthesized and the final amino group deblocked on a modified Expedite™ instrument (Millipore Corp., Bedford, Mass.). After the last linker synthesis cycle, the terminal t-BOC protecting group was removed with 95% trifluoracetic acid (TFA), 5% m-cresol for 5 min. followed by washing with DCM/DMF for 2 min. Just prior to coupling "on column" with the Biotin or Fluorescein XPP reagents, the support was washed with neat Pyridine. The modification reagents were made up in dry DMF to a final concentration of 0.1M and diisopropylethylamine (DIPEA) was then added to a final concentration of 0.2M. The HPP active ester reagent was then used to couple the resin containing the PNA (0.5 mg to 12 mg of support with 0.3–0.5 mole of reactive NH2 on the PNA) with Biotin or Fluorescein for 15 min. at room temperature. After coupling the support was washed with DCM/DMF and then removed from the reaction column into a Ultrafree™-MC device (Millipore Corp. cat. no. SE3P230J3) containing a PTFE membrane. The PNA was then cleaved from the support and the protecting groups removed in 20% trifluoromethanesulfonic acid (TFMSA), 70% TFA and 10%m-cresol for 2 hours at room temp. The resin was retained in the Ultrafree-MC device and the filtrate collected after centrifugation at 2000×G for 2–3 min. The labeled PNA was then precipitated from the acid cleavage solution by adding 1 ml of anhydrous ether and chilling on dry ice for 5 minutes. The heavy precipitate was collected by centrifugation at 2000×G for 5 minutes. After resuspending 2× in ether the pellet was allowed to air dry. The resulting material was then resuspended in a small volume of 0.1% aqueous TFA and subjected to mass spectrometric analysis using a prototye Matrix Assisted Laser Desorption Time of Flight Mass Spectrometer, run in positive ion mode, (Millipore Corp.) using sinapinic acid as a matrix and insulin as an internal mass standard at 5734.5 amu. All mass data was run under these conditions.

Figure 3:
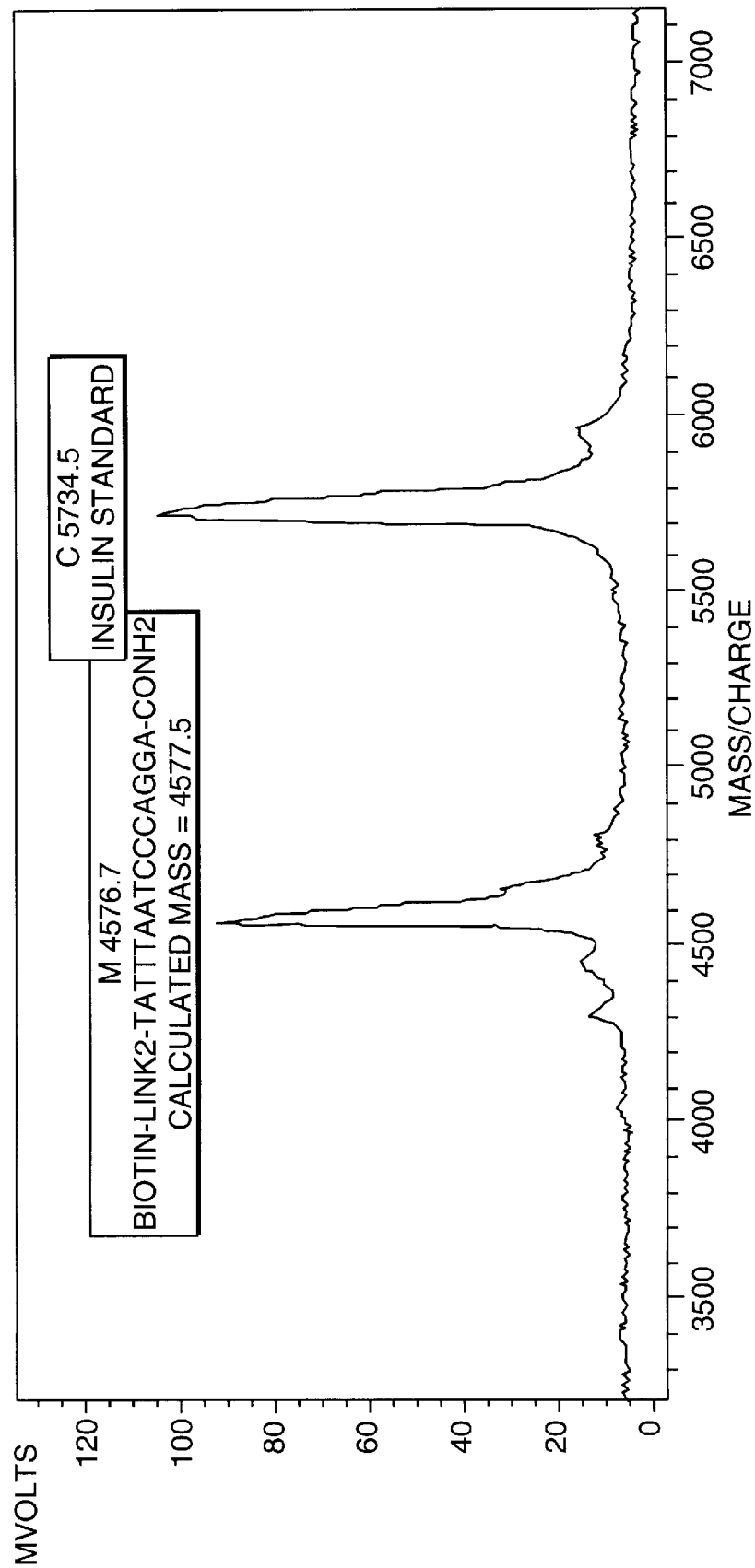
FIG. 3 is a mass spectrum of Biotin-[linker]2-TATTTAATCCCAGGA-CONH2 (SEQ ID NO: 1).

Results. After cleavage from the PEG polystyrene support the PNA molecules were routinely analyzed by mass spectrometry to confirm identity compared to a mass calculated from the known chemical structure of the molecule. An example of a PNA of sequence Biotin-[linker]2-TATTTAATCCCAGGA-CONH2 (SEQ ID No. 1) is shown in FIG. 3 with a measured mass of 4576.7 compared to an expected mass of 4577.5 confirming the addition of a Biotin structure to the molecule.

Figure 4:
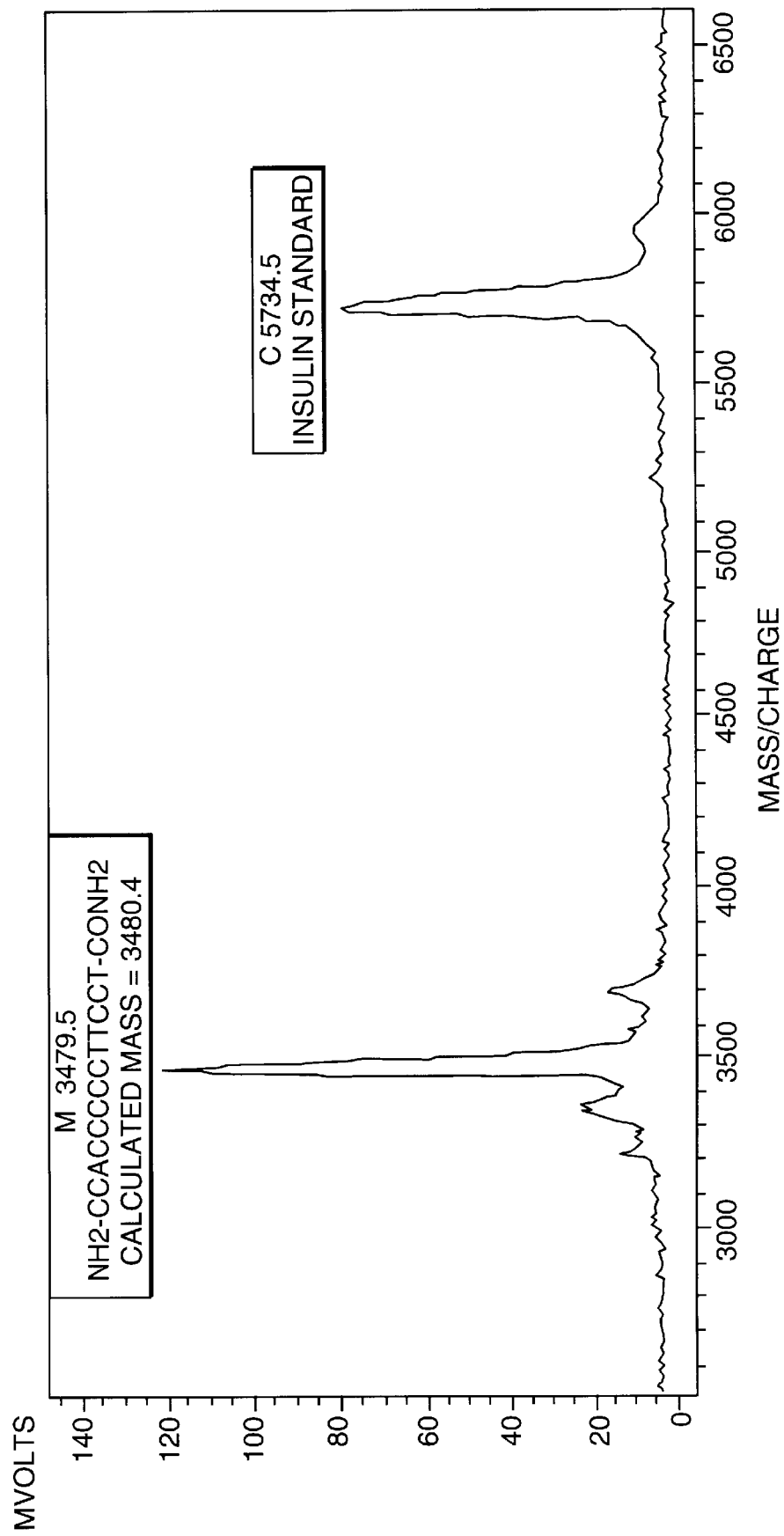
FIG. 4 is a mass spectrum of a PNA sequence NH2-CCACCCCTTCCT-CONH2 (SEQ ID NO: 2).
Figure 5:
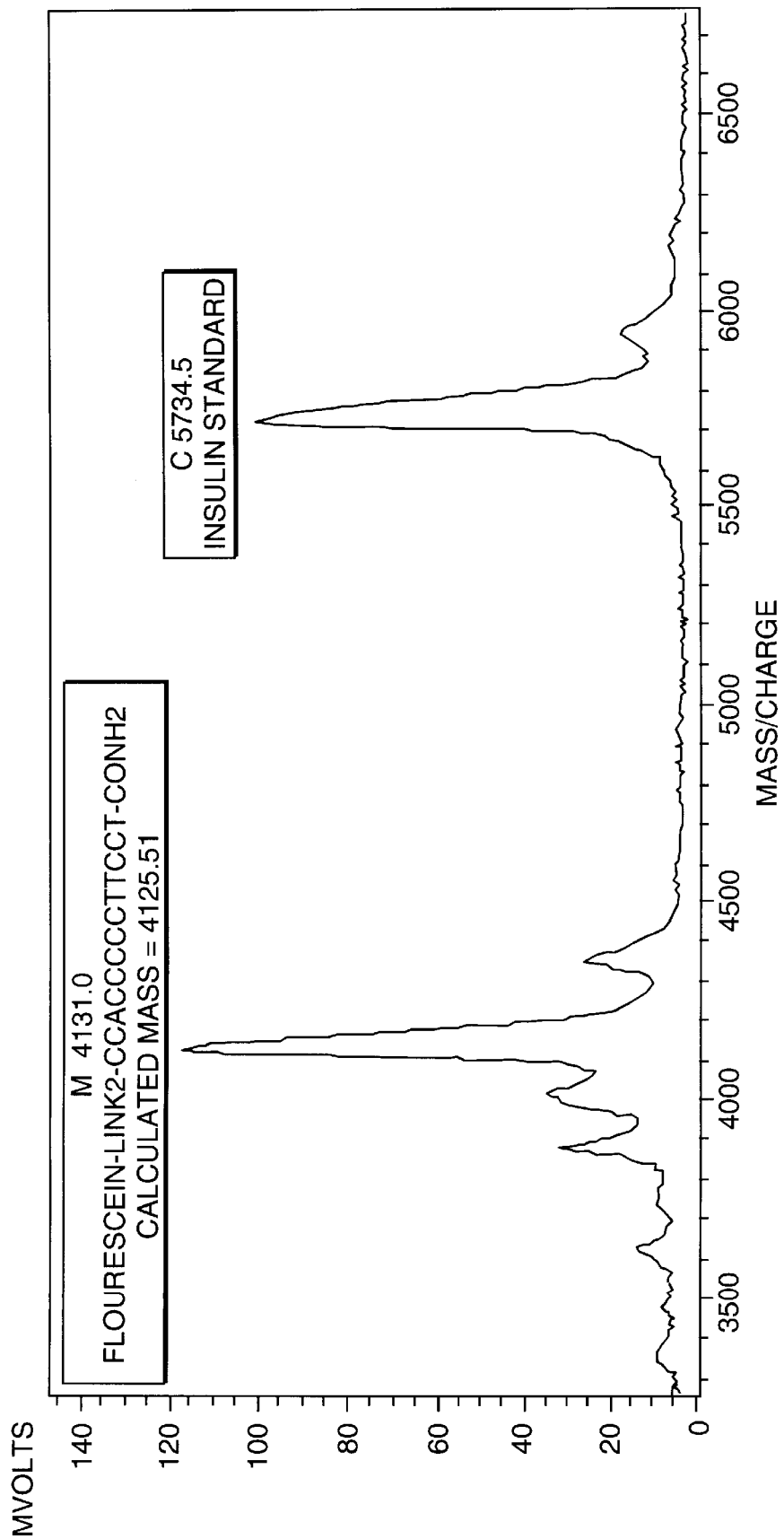
FIG. 5 is a mass spectrum of fluoresceinated PNA sequence Fluorescein-[linker] CACCCCCTTCCT-CONH2 (SEQ ID NO: 2).

In a second example, a PNA sequence, NH2-CCACCCCCTTCCT-CONH2 (SEQ ID No. 2), was cleaved from the synthesis support and gave a measured mass of 3479.5 amu compared to an expected mass of 3480.4 amu and is shown in FIG. 4. To the same sequence two additional linker molecules were added and the terminal NH2 group labeled with Fluorescein-HPP. The resulting PNA was cleaved from the resin and gave a measured mass of 4131.0 amu compared to an expected mass of 4125.5 and is shown in FIG. 5. This confirmed the addition of the two linkers and Fluorescein to the sequence shown in FIG. 4. In summary the Biotin and Fluorescein XPP labeling reagents were able to quantitatively modify the NH2 terminus of PNA molecules following the protocol as outlined above.

Example 4

Preparation of DMTr-Biotin-isopropylcarboxamide

The labeling of a secondary amine is shown in this example. A sample of DMTr-biotin-HPP (840 mg, 1.2 mmol) was dissolved in 3 mL acetonitrile and treated with 280 mg isopropylamine (4.75 mmol). After 15 minutes at room temperature, the solution was concentrated to dryness and purified on a short silica chromatography column to yield a single product, 600 mg. (97%). $^1$H NMR: ($CDCl_3$) 7.3–6.8 (m, Ar); 5.9 (d, CON$\underline{H}$); 4.3 (2m, 2H, bridgeheads); 3.75 (s, 6H, $(OCH_3)_2$); 3.0 (m, 1H, $\underline{H}$CHS); 2.4 (d, 1H, HC$\underline{H}$S); 1.8 (t, 2H, C$\underline{H}_2CO_2$); 1.5–1.2 (—$CH_2$—); 1.05 (d, 6H, CH(C$\underline{H}_3)_2$).

Example 5

Peptide Labeling with Biotin and Fluorescein HPP

Materials and Methods

Fmoc-amino acids and all other peptide synthesis reagents were obtained from Millipore Corporation. tert-Butyl protection was used for the side chains of Asp, Glu, Thr, and Tyr; t-butyl 1-carbonxyl (Boc), was used for Lys; 2,2,5,7,8-pentamethylchroma-6-sulfonyl (Pmc) was used for Arg; and triphenylmethyl (Trt) was used for Asn and Gln. The side chain of Trp was unprotected.

I. Peptide Synthesis-Standard Chain Elongation

Continuous flow solid-phase synthesis was carried out automatically using a Millipore (Bedford, Mass.) 9050 Plus PepSynthesizer™. The flow rate of the unit pump was set at 5.0 mL/min and the following synthetic protocol was used: Fmoc group deblocking with 2% 1,8-diazabicyclo[5.4.0]-undec-7-ene (DBU) and 2% piperidine in DMF (7 min.), DMF washing (12 min.), amino acid coupling (30 min.), and DMF washing (8 min.). Syntheses were carried out on Fmoc-PAL-PEG-PS (0.27 mmol/g) which was prepared according to a procedure described in the literature (Barany, et al., in *Peptides* 1992: *Proceedings of the 22nd European Peptide Symposium*, Schneider, C. H. and Eberle, A. N., eds., Escom, Leiden, 267–268). Four equivalents of Fmoc-amino acid, hydroxybenzotriazole (HOBE) and benzotriazoyl-1-yloxy-tris (1-pyrrolidinol)+phosphonium hexafluorophosphate (PyBOP) were dissolved to a final concentration of 0.3M with a solution of 0.6M DMF in DMF and delivered to the final growing peptide support.

II. Addition of Biotin/Fluorescein HPP

Labeling of the peptide resin was performed manually in a 5 mL polypropylene syringe fitted with a polyethylene disc. In a typical experiment, the peptide attached to the resin (50 mg peptide resin, 15 μmol peptide) was treated with four equivalents of biotin (or fluorescein) HPP for 1 hour at 25° C. The resin was washed with DMF (5×2 mL) and $CH_2Cl_2$ (3×2 mL) and dried in vacuo.

III. Cleavage Conditions

Peptide-resin samples were treated with TFA-anisole-β-mercaptoethanol (95:3:2) for 2 hours. The filtrates were collected and the resin was washed further with TFA. Cold ether was added to the combined extracts and the solution was cooled to −70° C. After removing the supernatant, the resulting precipitate was washed several times with cold ether, dissolved in acetic acid and lyophilized, before analysis by HPLC.

Figure 10:
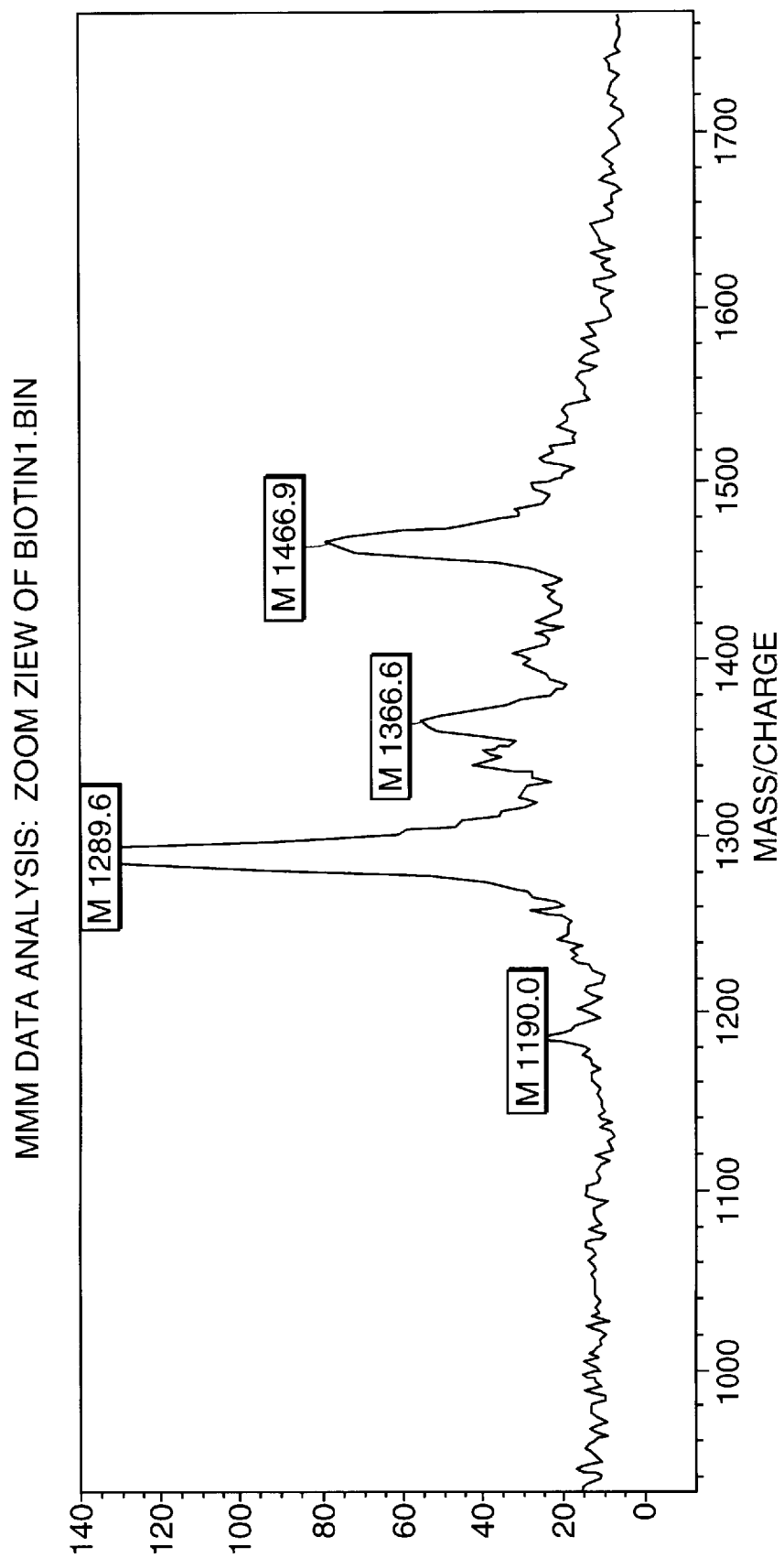
FIG. 10 is a mass spectrum of the biotinylated peptide having a calculated value of 1286 atomic mass units (amu), and a measured value of 1289.6 (amu).
Figure 11:
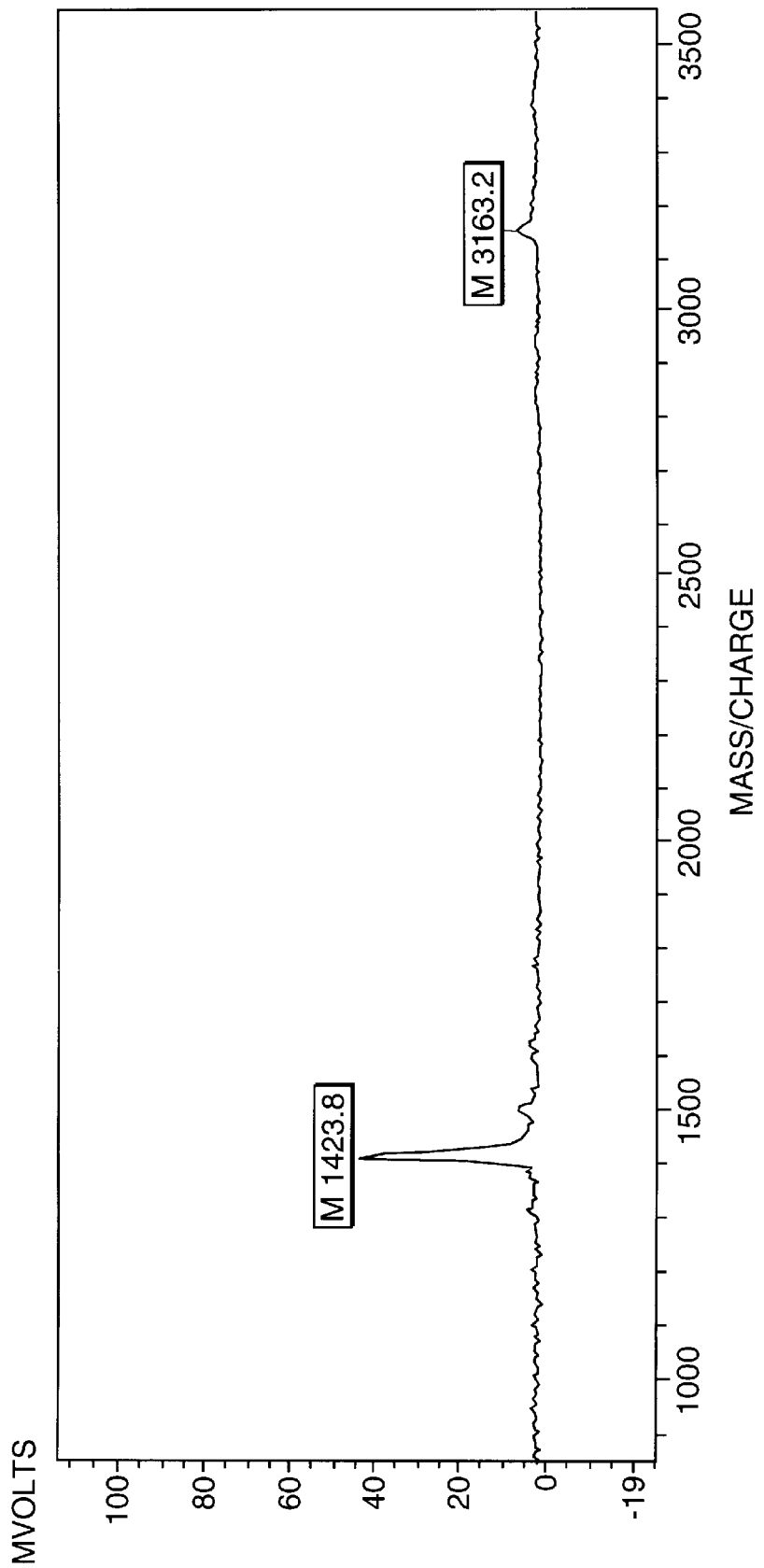
FIG. 11 is another mass spectrum, this one corresponding to the fluoresceinated peptide.

Peptide Sequence: H-Ala-Asn-Lys-Gly-Tyr(OAl)-Leu-Glu-Glu-Val-$NH_2$ (SEQ ID No. 3). FIG. 10 is a mass spectrum of the biotinylated peptide having a calculated value of 1286 amu, and a measured value of 1289.6 amu. This value is within the experimental error of the instrument, approximately ±0.3%. FIG. 11 is another mass spectrum, this one corresponding to the fluoresceinated peptide. The measured mass of 1423.8 amu is with the error range of the calculated value of 1419.8 amu.

Example 6

Specific Labeling of Oligodeoxynucleotides Using XP?-Fluorescein

This example shows the surprising specificity of the XPP-esters for amines over hydroxyls. An M13-OH forward primer of sequence (5'-3') AGGGTTTTCCCAGTCACGAC (SEQ ID No. 4) was prepared at 0.2 μmol scale on the Expedite™ 8909 Nucleic Acid Synthesizer (Millipore Corporation, Bedford, Mass.) using standard DNA protocols. The final DMTr group was removed. A second synthesis was done and after the final DMTr removal, the incipient oligonucleotide was coupled with N-monomethoxytrityl(MMTr)aminohexa-6-oxycyanoethyl-N,N-diisopropylamnino phosphoramidite (Millipore Corporation) in acetonitrile. Cleavage of the resulting 5'-MMTr group with 3% dichloroacetic acid in acetonitrile for 3 minutes afforded the same oligonucleotide as above, but containing a primary amine group at the 5' terminus (M13-NH2).

Figure 7A:
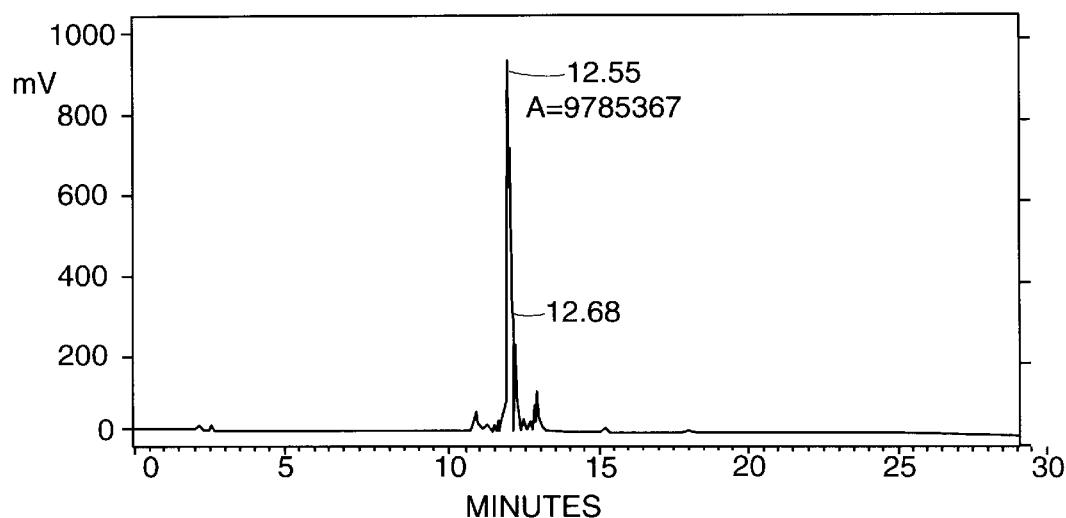
FIG. 7a is a liquid chromatography chromatogram of M13-NH2 peptide (260 nm).
Figure 7B:
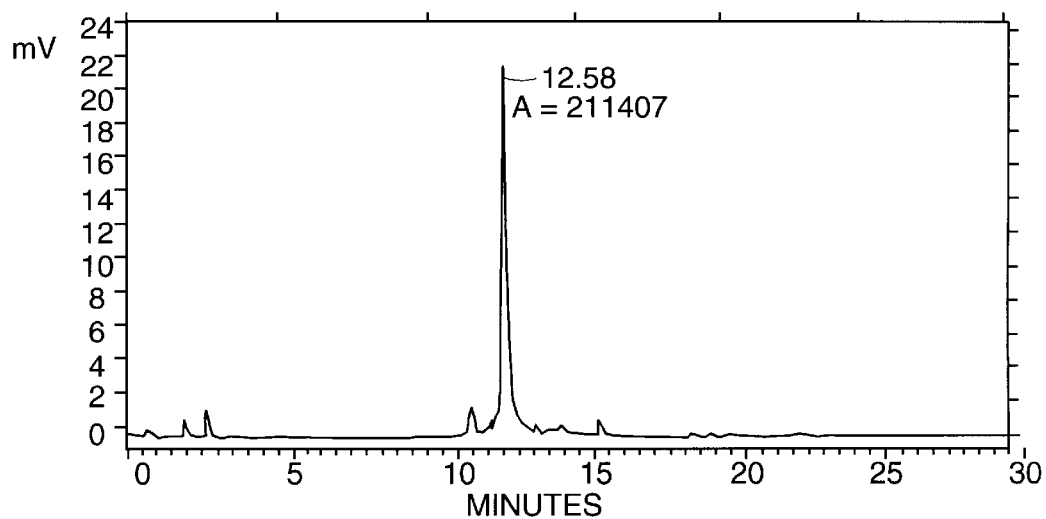
FIG. 7b is a liquid chromatography chromatogram of M13-OH (260 nm).
Figure 8A:
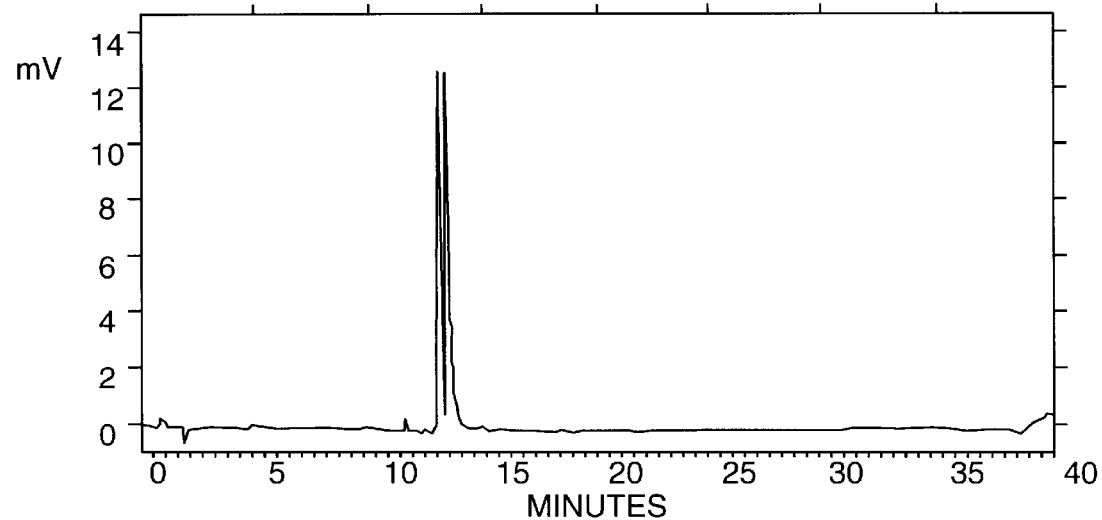
FIG. 8a is a liquid chromatography chromatogram of fluoresceinated M13-NH2 at 495 nm.
Figure 8B:
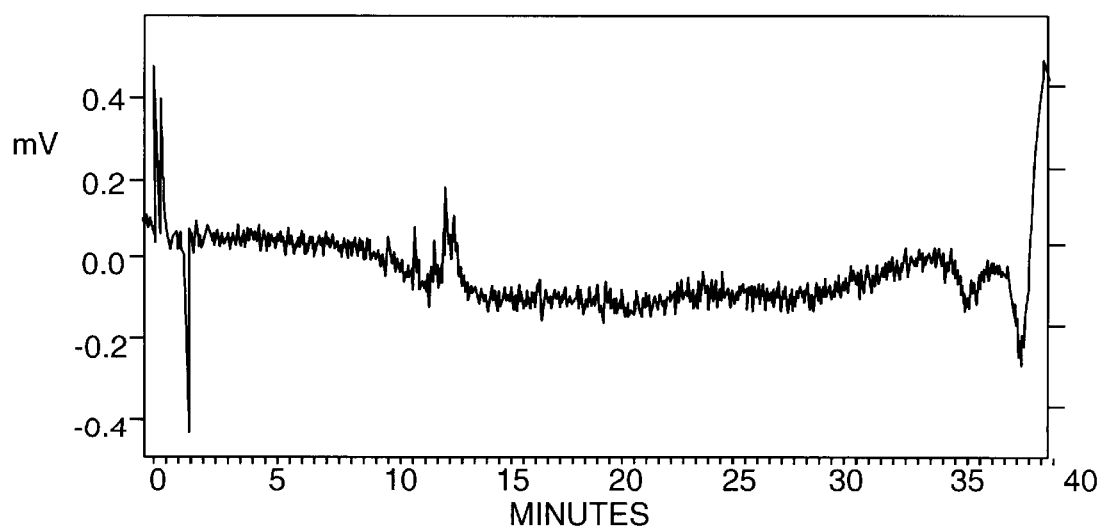
FIG. 8b is a liquid chromatography chromatogram of fluoresceinated M13-OH at 495 nm.
Figure 9:
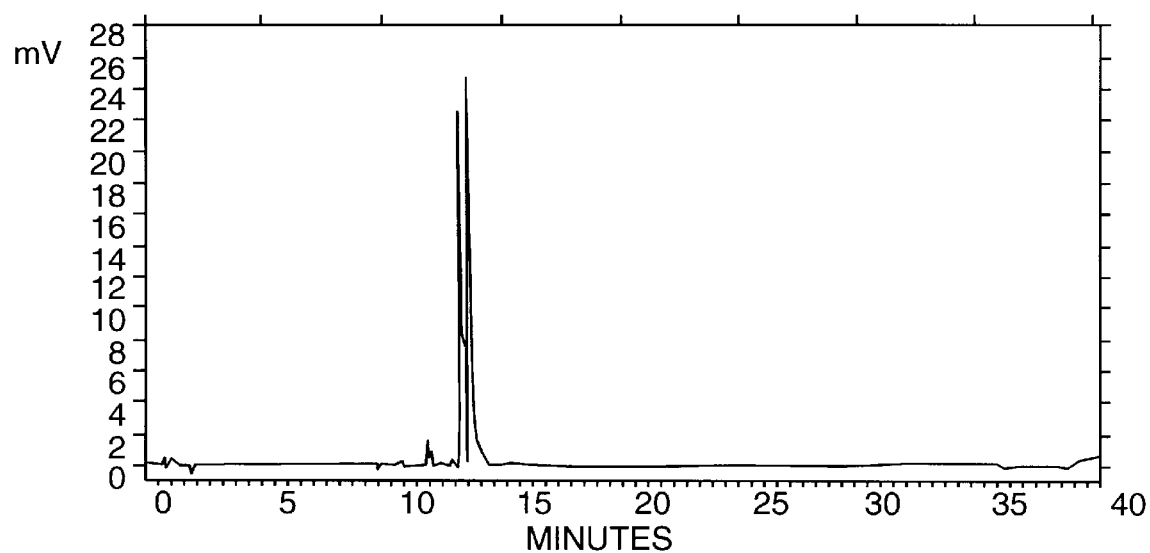
FIG. 9 is a liquid chromatography chromatogram of M13-OH and M13-NH2, both reacted with fluorescein-HPP, at 495 nm.

The labeling experiments were carried out to show the specificity of the activated ester. Samples of M13-OH and M13-NH2 were taken separately, as well as equal samples of the two together in one test tube. Samples of the support in 1.5 mL polypropylene tubes were treated separately with a solution of 5% triethylamine in acetonitrile, vortexed and centrifuged. The supernatants were removed and the support treated with 10 mM Fluorescein-HPP in acetonitrile. After 15 minutes, the solutions were removed and the support solids washed with 3×1 mL acetonitrile. The samples were then taken up in 750 microliter (μl) concentrated aqueous ammonia and warmed to 55° C. for 18 hours. The solids were removed by filtration and the filtrates frozen and lyophilized. The resulting pellets-were resuspended in distilled water and analyzed by HPLC. FIGS. 7–9 illustrate the reactions. FIGS. 7a and 7b are chromatograms of the starting materials M13-OH and M13-NH2 peptides, respectively, taken at 260 nm. FIGS. 8a and 8b are the same samples measured at 495 nm. Only fluorescent species will be visible at this wavelength. The absence of any signal in 8b shows that there is no significant labeling of the oligonucleotide that does not contain a free amine group. The pair of resolved isomers in FIG. 8a shows the two pivaloyl isomers. FIG. 9 shows the result of reacting both M13-NH2 and M13-OH with HPP-fluorescein together. FIG. 9 is indistinguishable from FIG. 8b, the M13-NH2 chromatogram.

Although the foregoing invention has been described by way of illustration and example for purposes of clarity and understanding, it will be obvious that certain changes and modifications may be practiced within the scope of the invention, as limited only by the scope of the appended claims.

---

We claim:

1. A pyrazolinone derivative having the formula:

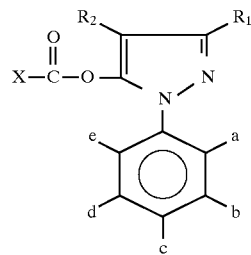

wherein $R_1$ is selected from the group consisting of H, methyl, ethyl, isopropyl, phenyl, nitrophenyl, chlorophenyl and benzyl;

$R_2$ is selected from the group consisting of H, methyl, ethyl, isopropyl, phenyl nitrophenyl, chlorophenyl, benzyl, halogen and $NO_2$;

a b, c, d and e are selected from the group consisting of H, $NO_2$, halogen and $SO_3H$, provided that at least one of a, b, c, d, and e is $NO_2$ or $SO_3H$; and X is selected from the group consisting of anthracene, acridine, benzofuran, BODIPY (4,4-difluoro-4-bora-3a,4a-diaza-s-indacene) and its derivatives, coumarin and its derivatives, digoxigenin, eosin, Lucifer Yellow, rhodamine and its derivatives, a steroid, a sulphonated aminonaphthalene, 1-anilinonaphthalene-8-sulfonic acid, 2-anilinonaphthalene-6-sulfonic acid, 8-aminonaphthalene-1,3,6-trisulfonic acid (ANTS), 8-aminonaphthalene-1,3-disulfonic acid, 8-anilinonaphthalene-1,6-disulfonic acid, and 8-aminonaphthalene-3,6-disulfonic acid.

2. A pyrazolinone derivative having the formula:

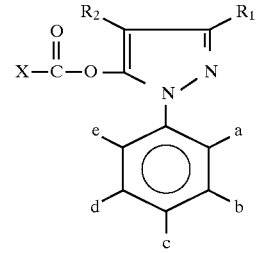

wherein $R_1$ is selected from the group consisting of H, methyl, ethyl, isopropyl, phenyl, nitrophenyl, chlorophenyl and benzyl;

$R_2$ is selected from the group consisting of H, methyl, ethyl, isopropyl, phenyl nitrophenyl, chlorophenyl, benzyl, halogen and $NO_2$;

a, b, c, d and e are selected from the group consisting of H, $NO_2$, halogen and $SO_3H$, provided that at least one of a, b, c, d, and e is $NO_2$ or $SO_3H$; and X—$CO_2$— is a moiety selected from the group consisting of biotin, dimethoxytritylbiotin, fluorescein and dipivaloylcarboxyfluorescein.

3. The pyrazolinone derivative of claim 2 wherein X—$CO_2$— is a biotin moiety;
$R_1$, $R_2$, a, b, c, d, and e are H; and
c is $NO_2$.

4. The pyrazolinone derivative of claim 2 wherein X—$CO_2$—is a 4,4'-dimethoxytriylbiotin moiety;
$R_1$, $R_2$, a, b, c, d, and e are H, and
c is $NO_2$.

5. The pyrazolinone derivative of claim 2 wherein X—$CO_2$— is a dipivaloylcarboxyfluorescein moiety;
$R_1$, $R_2$, a, b, c, d, and e are H; and
c is $NO_2$.

6. A method for detectably labeling an amine-functionalized molecule comprising
reacting the pyrazolinone derivative of claim 1, 3, 4, 5 or 2 with an amine-functionalized molecule.

* * * * *

UNITED STATES PATENT AND TRADEMARK OFFICE
CERTIFICATE OF CORRECTION

PATENT NO.  : 5,859,259
DATED       : Jan. 12, 1999
INVENTOR(S) : Sinha et al.

It is certified that error appears in the above-identified patent and that said Letters Patent is hereby corrected as shown below:

At column 9, line 32, "polyethyleneglyco/(PEG)-polystyrene" should read
    --polyethyleneglycol(PEG)-polystyrene--.
At column 11, line 9, "t-butyl 1-carbonxyl" should read --t-butyloxycarbonyl--.
At column 11, line 10, "8-pentamethylchroma-6-sulfonyl" should read –8-pentamethylchroman-6-
    sulfonyl--.
At column 11, line 29, "(HOBE)" should read --(HOBt)--.
At column 11, line 30, "benzotriazoyl-1-yloxy-tris (1-pyrrolidinol)+phosphonium" should read --
    benzotriazol-1-yloxy-tris(1-pyrrolidinol)-phosphonium--.
At column 12, line 9, "XP?-Fluorescein" should read –XPP-Fluorescein--.
In claim 2, column 16, line 30, "phenyl nitrophenyl" should read --phenyl, nitrophenyl--.
In claim 4, column 16, line 41, "4,4'-dimethoxytriylbiotin" should read --4,4'-
    dimethoxytritylbiotin--.

Signed and Sealed this

Seventh Day of March, 2000

*Attest:*

Q. TODD DICKINSON

*Attesting Officer*     Commissioner of Patents and Trademarks

UNITED STATES PATENT AND TRADEMARK OFFICE
CERTIFICATE OF CORRECTION

PATENT NO. : 5,859,259
DATED : January 12, 1999
INVENTOR(S) : Sinha et al.

It is certified that error appears in the above-identified patent and that said Letters Patent is hereby corrected as shown below:

Column 4,
Line 45, "HPP-reporter" should read -- XPP-reporter --.

Signed and Sealed this

Second Day of October, 2001

Attest:

NICHOLAS P. GODICI
Attesting Officer *Acting Director of the United States Patent and Trademark Office*